United States Patent
Maile et al.

(10) Patent No.: US 11,864,928 B2
(45) Date of Patent: Jan. 9, 2024

(54) SYSTEMS AND METHODS TO DETECT RESPIRATORY DISEASES USING RESPIRATORY SOUNDS

(71) Applicant: Cardiac Pacemakers, Inc., St. Paul, MN (US)

(72) Inventors: Keith R. Maile, New Brighton, MN (US); Pramodsingh Hirasingh Thakur, Woodbury, MN (US); Michael J. Kane, Roseville, MN (US); Bin Mi, Plymouth, MN (US); Ron A. Balczewski, Bloomington, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 950 days.

(21) Appl. No.: 15/603,772

(22) Filed: May 24, 2017

(65) Prior Publication Data

US 2017/0347968 A1    Dec. 7, 2017

Related U.S. Application Data

(60) Provisional application No. 62/344,054, filed on Jun. 1, 2016.

(51) Int. Cl.
*A61B 5/00* (2006.01)
*A61N 1/36* (2006.01)
(Continued)

(52) U.S. Cl.
CPC .......... *A61B 5/7282* (2013.01); *A61B 5/0022* (2013.01); *A61B 5/08* (2013.01);
(Continued)

(58) Field of Classification Search
None
See application file for complete search history.

(56) References Cited

U.S. PATENT DOCUMENTS

| | | | | |
|---|---|---|---|---|
| 5,309,922 A | * | 5/1994 | Schechter | A61B 7/003 600/534 |
| 6,443,907 B1 | * | 9/2002 | Mansy | A61B 7/04 600/529 |

(Continued)

FOREIGN PATENT DOCUMENTS

| | | |
|---|---|---|
| JP | 2012205693 A | 10/2012 |
| WO | WO-2017210053 A1 | 12/2017 |

OTHER PUBLICATIONS

Jané, R., et al. "Spectral analysis of respiratory sounds to assess bronchodilator effect in asthmatic patients." Proceedings of the 20th Annual International Conference of the IEEE Engineering in Medicine & Biology Society. vol. 20 Biomedical Engineering Towards the Year 2000 and Beyond, vol. 6, IEEE (Year: 1998).*

(Continued)

*Primary Examiner* — Jacqueline Cheng
*Assistant Examiner* — Jairo H Portillo
(74) *Attorney, Agent, or Firm* — Schwegman Lundberg & Woessner, P.A.

(57) ABSTRACT

Systems and methods for monitoring patients with respiratory diseases are described. A system may include a sensor circuit configured to sense one or more physiological signals indicative of respiratory sounds, and a spectral analyzer to generate first and second spectral contents at respective first and second frequency bands. The system may produce a respiratory anomaly indicator using the first and second spectral contents, or additionally with other physiological parameters. The system may detect an onset or progression of a target respiratory condition such as asthma or chronic (Continued)

obstructive pulmonary disease using the respiratory anomaly indicator, or to trigger or adjust a therapy.

19 Claims, 5 Drawing Sheets

(51) Int. Cl.
*A61N 1/365* (2006.01)
*A61B 5/08* (2006.01)
*A61B 7/00* (2006.01)
*A61B 7/02* (2006.01)
*A61B 7/04* (2006.01)

(52) U.S. Cl.
CPC .......... *A61B 5/4836* (2013.01); *A61B 5/7246* (2013.01); *A61B 5/7264* (2013.01); *A61B 7/003* (2013.01); *A61B 7/023* (2013.01); *A61B 7/04* (2013.01); *A61N 1/3601* (2013.01); *A61N 1/3611* (2013.01); *A61N 1/36514* (2013.01); *A61B 2562/0219* (2013.01)

(56) References Cited

U.S. PATENT DOCUMENTS

| | | | |
|---|---|---|---|
| 6,949,075 B2 | 9/2005 | Hatlestad et al. | |
| 2004/0127807 A1 | 7/2004 | Hatlestad et al. | |
| 2006/0020294 A1* | 1/2006 | Brockway | A61B 7/00 607/17 |
| 2006/0056641 A1* | 3/2006 | Nadjar | A61B 7/04 381/67 |
| 2006/0074334 A1* | 4/2006 | Coyle | A61B 5/369 600/534 |
| 2006/0077063 A1 | 4/2006 | Cheng et al. | |
| 2008/0071185 A1* | 3/2008 | Beck | A61B 5/0816 600/529 |
| 2008/0232605 A1* | 9/2008 | Bagha | A61B 7/04 381/67 |
| 2008/0312547 A1* | 12/2008 | Wada | A61B 5/11 600/534 |
| 2010/0168812 A1* | 7/2010 | Blomqvist | A61B 5/02405 607/17 |
| 2011/0125044 A1* | 5/2011 | Rhee | A61B 5/113 600/534 |
| 2011/0218454 A1* | 9/2011 | Low | A61B 5/4812 600/544 |
| 2013/0060150 A1* | 3/2013 | Song | A61N 1/3627 600/484 |
| 2015/0087930 A1* | 3/2015 | Cho | A61B 5/6892 600/301 |
| 2016/0022204 A1* | 1/2016 | Mostov | A61B 5/0002 600/301 |
| 2016/0235344 A1* | 8/2016 | Auerbach | A61B 5/087 |
| 2016/0296588 A1* | 10/2016 | Hill | A61P 35/00 |
| 2017/0325717 A1* | 11/2017 | Dellimore | A61B 5/0823 |

OTHER PUBLICATIONS

Chamberlain, Daniel, et al. "Mobile stethoscope and signal processing algorithms for pulmonary screening and diagnostics." 2015 IEEE Global Humanitarian Technology Conference (GHTC). IEEE, 2015. (Year: 2015).*

Habukawa, Chizu, et al. "A new modality using breath sound analysis to evaluate the control level of asthma." Allergology International 62.1 (2013): 29-35. (Year: 2013).*

Jardin, Francois, et al., "Mechanism of Paradoxic Pulse in Bronchial Asthma", Circulation, 66, No. 4, [Online]. Retrieved from the Internet: <URL: http://circ.ahajournals.org/, (Oct. 1982), 887-894.

Pasterkamp, Hans, et al., "Respiratory Sounds—Advances Beyond the Stethoscope", Am I Respir Crit Care Med, vol. 156, (1997), 974-987.

"International Application Serial No. PCT/US2017/034171, International Preliminary Report on Patentability dated Dec. 13, 2018", 8 pgs.

"International Application Serial No. PCT/US2017/034171, International Search Report dated Sep. 25, 2017", 4 pgs.

"International Application Serial No. PCT/US2017/034171, Written Opinion dated Sep. 25, 2017", 8 pgs.

* cited by examiner

SYSTEMS AND METHODS TO DETECT RESPIRATORY DISEASES USING RESPIRATORY SOUNDS

CLAIM OF PRIORITY

This application claims the benefit of priority under 35 U.S.C. § 119(e) of U.S. Provisional Patent Application Ser. No. 62/344,054, filed on Jun. 1, 2016, which is herein incorporated by reference in its entirety.

TECHNICAL FIELD

This document relates generally to medical devices, and more particularly, to systems and methods for monitoring patients with a respiratory disease.

BACKGROUND

Asthma and chronic obstructive pulmonary disease (COPD) are common chronic respiratory conditions that may affect a large population. Although asthma affects people of all ages, children and adolescents are disproportionately affected by the disease compared to other age groups. Asthma is caused by inflammation and tightening of the airway muscles, which narrows the airways. COPD is a progressive respiratory disease that may be characterized by decreased airflow over time, as well as inflammation of the tissues that line the airway. COPD include two main conditions, namely emphysema and chronic bronchitis. COPD is one of the major comorbidities in patients with chronic diseases such as congestive heart failure (CHF), which is a leading cause of death in the United States.

Asthma and COPD may coexist in some patients. About 40% of COPD patients also have asthma. In addition, asthma is considered a clinical risk factor for developing COPD. Both asthma and COPD, among some other respiratory diseases, may have similar symptoms, which may include chronic coughing, wheezing, shortness of breath, or hyper-responsiveness to airflow during inspiration, among others. Compared to patients with COPD, lung function is only fully reversible in patients with asthma.

Respiratory sounds may contain information about physiologies and pathologies of lungs and airways obstruction. Distinction between normal respiratory sounds and abnormal ones may be used for diagnosing respiratory diseases such as asthma or COPD. Abnormal respiratory sounds may include continuous or stationary sounds such as wheezes and rhonchus, or discontinuous or non-stationary sounds such as fine or coarse crackles. Wheezing indicates that the airway is narrowed, either by a solid mass, mucus plug, bronchospasm or bronchial wall swelling, and may sound more musical in nature than normal breathing sounds. Asthma and COPD are most common causes of wheezing.

Respiratory diseases such as asthma and COPD may have a huge economic impact on the healthcare system. Proper monitoring of patient with respiratory diseases such as asthma or COPD may improve the accuracy and reliability in detecting restrictive or obstructive respiratory conditions prior to needing an inhaler or to administer appropriate therapies to prevent worsening of respiratory conditions, thereby reducing healthcare cost associated with the treatment and hospitalization.

SUMMARY

Analyzing the respiratory sounds may indicate the state of the lungs parenchyma, the dimension of the airways and their pathological modification. Auscultation of the chest in a clinical examination remains to be an invaluable clinical tool and a common method of evaluating respiratory sounds. However, auscultation may not be feasible for patients in ambulatory settings. The present inventors have recognized that there remains a need for systems, devices, and methods for identifying, characterizing, or diagnosing respiratory disorders particularly in an ambulatory setting with the use of information in respiratory sounds.

This document discusses, among other things, a patient management system for monitoring patients with respiratory diseases. In addition to asthma and COPD, systems and methods discussed in this document may also be suitable for monitoring patients with various sorts of acute and chronic respiratory diseases, including obstructive or restrictive lung diseases such as emphysema, COPD, pulmonary fibrosis, or sarcoidosis, among many others. A system as described in this document may include a sensor circuit to sense one or more physiological signals indicative of respiratory sounds, and a spectral analyzer to generate first and second spectral contents at respective first and second frequency bands. The system may produce a respiratory anomaly indicator using the first and second spectral contents, or additionally with other physiological parameters. The respiratory anomaly indicator may be used to detect an onset or progression of a target respiratory condition such as asthma or COPD, or to trigger or adjust a therapy.

Example 1 is a system for managing a respiratory disease in a patient. The system may comprise: a sensor circuit including a sense amplifier coupled to at least one physiological sensor to sense one or more physiological signals indicative of respiratory sounds; a signal processor circuit including a spectral analyzer circuit configured to generate from the sensed one or more physiological signals a first spectral content within a first frequency band and a second spectral content within a second frequency band, the second frequency band having a higher center frequency than the first frequency band; a detector circuit coupled to the signal processor circuit and configured to generate a respiratory anomaly indicator using the first spectral content relative to the second spectral content; and an output circuit configured to provide the respiratory anomaly indicator to a user or a process. The respiratory anomaly indicator may indicate status of a target respiratory condition.

In Example 2, the subject matter of Example 1 optionally includes the output circuit that may be configured to generate a command signal to trigger or adjust a therapy delivered to the patient.

In Example 3, the subject matter of any one or more of Examples 1-2 optionally includes the at least one physiological sensor that has a frequency response over a bandwidth including the first and second frequency bands.

In Example 4, the subject matter of any one or more of Examples 1-3 optionally includes the at least one physiological sensor that is configured to selectably operate in a first operating mode or a second operating mode. The spectral analyzer circuit may be configured to generate the first spectral content when the at least one physiological sensor operates in the first operating mode, and to generate the second spectral content when the least one physiological sensor operates in the first operating mode.

In Example 5, the subject matter of any one or more of Examples 1-4 optionally includes the sensor circuit that may include an accelerometer sensor configured to sense an acceleration signal and a microphone sensor configured to sense an acoustic signal. The spectral analyzer circuit may be configured to generate the first spectral content from the acceleration signal, and to generate the second spectral content from the acoustic signal.

In Example 6, the subject matter of any one or more of Examples 1-5 optionally includes the at least one physiological sensor which may be a wearable or implantable sensor configured to be worn on or implanted at the patient's thorax or abdomen.

In Example 7, the subject matter of any one or more of Examples 1-6 optionally comprises a respiratory sensor circuit that may be configured to sense a respiration signal and to detect a respiratory phase within a respiratory cycle. The spectral analyzer circuit may generate the first and second spectral contents using the sensed one or more physiological signals during the detected respiratory phase.

In Example 8, the subject matter of Example 7 optionally includes the detector circuit that may further be configured to generate a correlation between the sensed one or more physiological signals and the respiration signal during a specified respiratory phase, and classify the respiratory disease into one of two or more categories of pulmonary distress using the correlation.

In Example 9, the subject matter of any one or more of Examples 1-8 optionally includes the spectral analyzer circuit that may generate the first spectral content within the first frequency band of approximately 100-300 Hz, and the second spectral content within the second frequency band of approximately 800-1200 Hz.

In Example 10, the subject matter of any one or more of Examples 1-9 optionally includes the respiratory anomaly indicator that may include a spectral power ratio of one of the first or second spectral content to the other of the first or second spectral content.

In Example 11, the subject matter of any one or more of Examples 1-10 optionally includes a memory circuit to store a reference spectral content of respiratory sounds including a first reference spectrum within the first frequency band and a second reference spectrum within the second frequency band. The detector circuit may be configured to generate the respiratory anomaly indicator further using the reference spectral content.

In Example 12, the subject matter of Example 11 optionally includes the detector circuit that may generate the respiratory anomaly indicator in response to: the first spectral content having a lower spectral power than the first reference spectrum by a specified margin; the second spectral content having a higher spectral power than the second reference spectrum by a specified margin; or a ratio of the first spectral content to the second spectral content falling below a ratio of the first reference spectrum to the second reference spectrum by a specified margin.

In Example 13, the subject matter of any one or more of Examples 11-12 optionally includes the sensor circuit that may be configured to establish a baseline respiratory sounds signal. The signal processor circuit may be configured to generate from the baseline respiratory sounds signal the first and second reference spectra.

In Example 14, the subject matter of any one or more of Examples 1-13 optionally includes a physical activity sensor configured to sense the patient's physical activity intensity. The detector circuit may be configured to trend over time the first or second spectral content of the respiratory sounds and the physical activity intensity, and generate the respiratory anomaly indicator using co-variation between the trended first or second spectral content of the respiratory sounds and the trended physical activity intensity.

In Example 15, the subject matter of Example 14 optionally includes the detector circuit that may be configured to generate the co-variation indicator which may include: a ratio of the intensity of the first or second spectral contents of the respiratory sounds to the physical activity intensity; a time interval between a peak of the intensity of the first or second spectral contents of the respiratory sounds and a peak of the physical activity intensity; or a ratio of the respiratory anomaly indicator to the physical activity intensity.

Example 16 is a method for detecting a respiratory anomaly in a patient using a respiratory disease management system. The method comprises steps of: sensing, via an implantable or wearable physiological sensor, one or more physiological signals indicative of respiratory sounds; performing spectral analysis, via a spectral analyzer, on the sensed one or more physiological signals to generate a first spectral content within a first frequency band and a second spectral content within a second frequency band, the second frequency band having a higher center frequency than the first frequency band; and generating a respiratory anomaly indicator using the first spectral content relative to the second spectral content, the respiratory anomaly indicator indicating a status of a target respiratory condition; and providing the respiratory anomaly indicator to a user or a process.

In Example 17, the subject matter of Example 16 optionally includes a step of generating a signal to trigger or adjust a therapy delivered to the patient.

In Example 18, the subject matter of any one or more of Examples 16-17 optionally includes the spectral analysis that may include steps of: configuring the physiological sensor to operate in a first operating mode and generating the first spectral content when the sensor operates in the first operating mode; configuring the physiological sensor to operate in a different second operating mode and generating the second spectral content when the physiological sensor operates in the second operating mode.

In Example 19, the subject matter of any one or more of Examples 16-18 optionally includes steps of: sensing the one or more physiological signals that may include sensing an acceleration signal via a accelerometer sensor and an acoustic signal via a microphone sensor; performing the spectral analysis that may include generating the first spectral content from the acceleration signal and generating the second spectral content from the acoustic signal.

In Example 20, the subject matter of any one or more of Examples 16-19 optionally includes sensing a respiration signal and detecting a respiratory phase within a respiratory cycle. The spectral analysis may include generating the first and second spectral contents using the sensed one or more physiological signals during the detected respiratory phase.

In Example 21, the subject matter of Example 20 optionally includes steps of generating a correlation between the sensed one or more physiological signals and the respiration signal during a specified respiratory phase, and classifying the respiratory disease into one of two or more categories of pulmonary distress using the correlation.

In Example 22, the subject matter of any one or more of Examples 16-21 optionally includes the respiratory anomaly indicator that may include a spectral power ratio of one of the first or second spectral content to the other of the first or second spectral content.

In Example 23, the subject matter of any one or more of Examples 16-22 optionally includes generating a reference spectral content of respiratory sounds. The reference spectral content may include a first reference spectrum within the first frequency band and a second reference spectrum within the second frequency band. The respiratory anomaly indicator may be generated in response to: the first spectral content having a lower spectral power than the first reference spectrum by a specified margin; the second spectral content having a higher spectral power than the second reference spectrum by a specified margin; or a ratio of the first spectral content to the second spectral content falling below a ratio of the first reference spectrum to the second reference spectrum by a specified margin.

In Example 24, the subject matter of any one or more of Examples 16-23 optionally includes steps of: sensing the patient's physical activity intensity; trending over time the first or second spectral contents of the respiratory sounds and the physical activity intensity; and generating the respiratory anomaly indicator using co-variation between the trended first or second spectral content of the respiratory sounds and the trended physical activity intensity.

The systems, devices, and methods discussed in this document may improve the medical technology of automated monitoring of patients with respiratory disease. The detection of respiratory anomaly based on spectral content of the respiratory sounds may enhance the performance and functionality of a medical system or an ambulatory medical device for detecting respiratory disease. In certain examples, the enhanced device functionality may include more timely detection of respiratory anomaly with increased accuracy at little to no additional cost. The improvement in system performance and functionality, provided by the present systems and methods, can reduce healthcare costs associated with management and hospitalization of patients with respiratory disease. The systems, devices, and methods discussed in this document also allow for more efficient device memory usage, such as by storing spectral contents or statistics of the spectral content of the respiratory sounds that are clinically more relevant to diagnosis of respiratory disease. As fewer false positive detections are provided, device battery life can be extended, fewer unnecessary drugs and procedures may be scheduled, prescribed, or provided, and an overall system cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring patients with respiratory diseases. The system may sense a signal indicative of respiratory sounds and determine spectral contents at different frequency bands. A respiratory anomaly indicator based at least on the spectral contents at different frequency bands may be generated and used for detecting an onset or progression of a target respiratory condition such as asthma or COPD, or to trigger or adjust a therapy.

Figure 1:
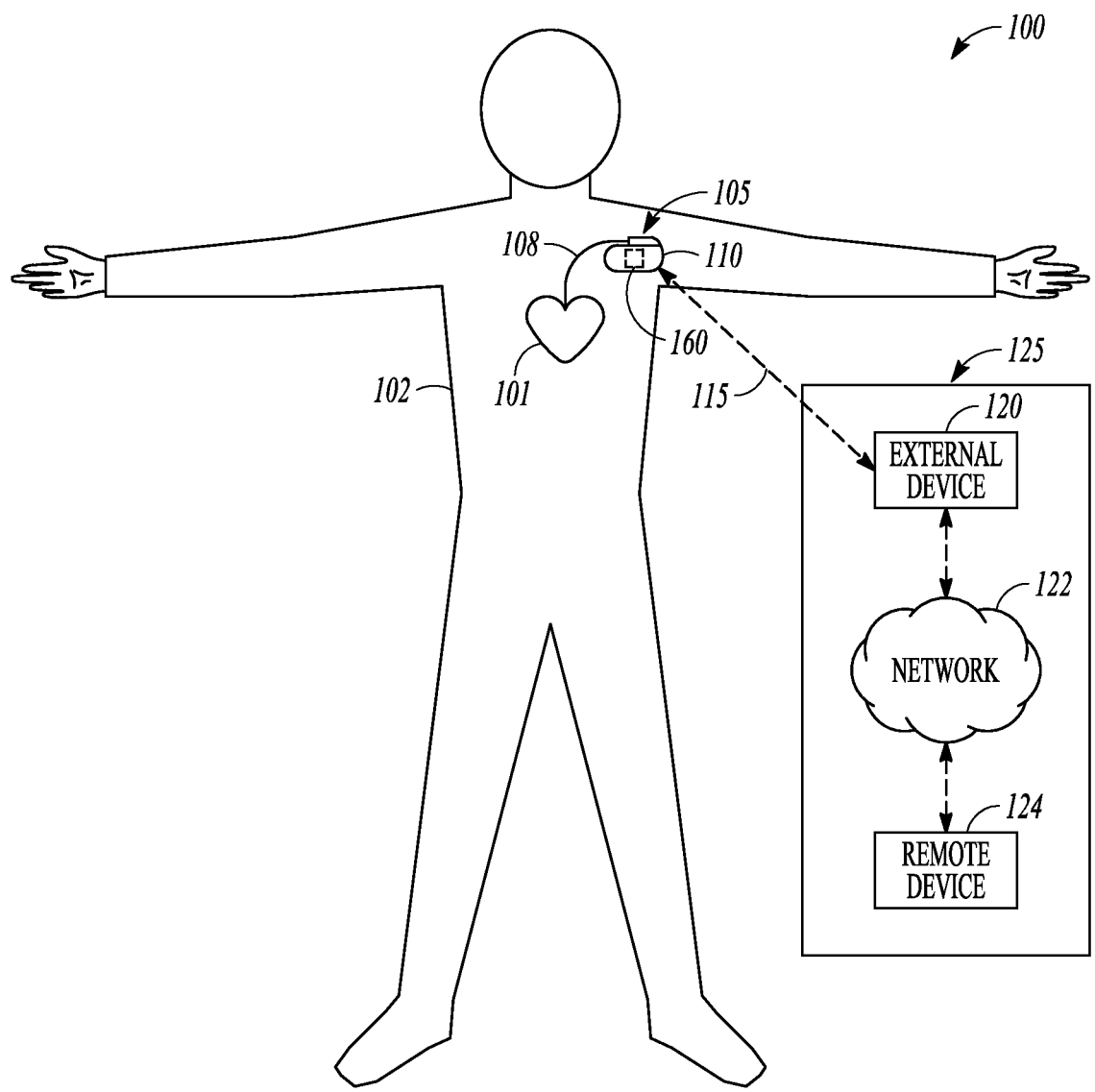
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may include an ambulatory system 105 associated with a patient body 102, an external system 125, and a telemetry link 115 providing for communication between the ambulatory system 105 and the external system 125.

The ambulatory system 105 may include an ambulatory medical device (AMD) 110 and a therapy delivery system such as a lead system 108. The AMD 110 may include an implantable device that may be implanted within the body 102 and coupled to a heart 101 via the lead system 108. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 may alternatively or additionally include subcutaneously implanted devices such as a subcutaneous ICD or a subcutaneous diagnostic device, wearable medical devices, or other external monitoring or therapeutic medical devices such as a bedside monitor.

The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the electrodes on the lead system 108 may be positioned inside or on a surface of at least a portion of the heart, such as a right atrium (RA), a right ventricle (RV), a left atrium (LA), a left ventricle (LV), or any tissue between or near the heart portions. In an example, the lead system 108 and the associated electrodes may be implanted subcutaneously or wearable on the patient body. The associated electrodes on the lead system 108 may be positioned at the patient's thorax or abdomen to sense intrinsic physiological signals indicative of cardiac or pulmonary activities, or physiological responses to diagnostic or therapeutic stimulations to a target tissue.

The AMD 110 may house an electronic circuit for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature. The AMD 110 may initiate or adjust therapies based on the sensed physiological signals.

The patient management system 100 may include a respiratory monitor 160 for monitoring patient respiration. The respiratory monitor 160 may analyze the diagnostic data such as acquired by the ambulatory system 105 for patient monitoring, risk stratification, and detection of events, indicating presence, onset, termination, improvement, or worsening of a target respiratory condition. Examples of the respiratory conditions may include wheezing, asthma, bronchoconstriction, COPD, bronchiectasis, acute bronchitis, pulmonary fibrosis, pneumoconiosis, acute respiratory distress syndrome, or sleep apnea. By way of non-limiting example and as illustrated in FIG. 1, the respiratory monitor 160 may be substantially included in the AMD 110. Alternatively, the respiratory monitor 160 may be substantially included in the external system 125, or be distributed between the ambulatory system 105 and the external system 125.

The external system 125 may be used to program the AMD 110. The external system 125 may include a programmer, or a patient management system that may access the ambulatory system 105 from a remote location and monitor patient status and/or adjust therapies. By way of non-limiting example, the external system 125 may include an external device 120 in proximity of the AMD 110, a remote device 124 in a location relatively distant from the AMD 110, and a telecommunication network 122 linking the external device 120 and the remote device 124. The telemetry link 115 may be an inductive telemetry link, a capacitive telemetry link, or a radio-frequency (RF) telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more of acquiring physiological data, performing at least one self-diagnostic test (such as for a device operational status), analyzing the physiological data to generate respiratory diagnostics such as presence or worsening of a target respiratory condition, or delivering at least one therapy to treat a respiratory disease.

Portions of the AMD 110 or the external system 125 may be implemented using hardware, software, or any combination of hardware and software. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
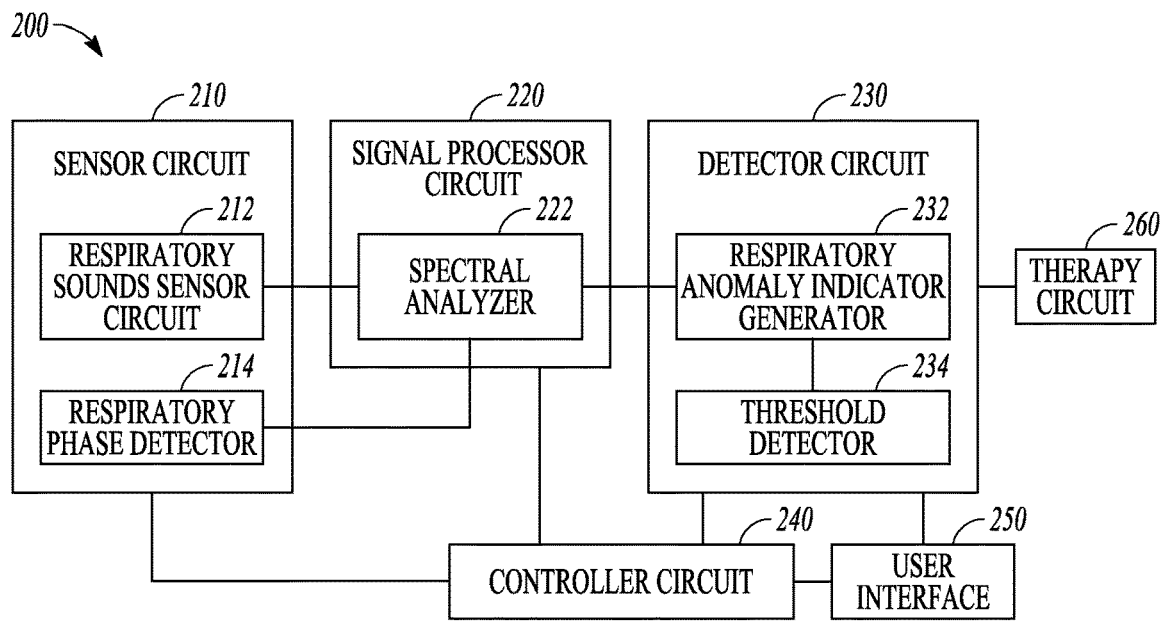
FIG. 2 illustrates generally an example of a respiratory monitoring system 200 for monitoring respiration and detecting respiratory anomaly.

FIG. 2 illustrates generally an example of a respiratory monitoring system 200 for monitoring respiration and detecting respiratory anomaly, such as wheezing, asthma, bronchoconstriction, COPD, bronchiectasis, acute bronchitis, pulmonary fibrosis, pneumoconiosis, acute respiratory distress syndrome, or sleep apnea. The respiratory monitoring system 200 may include one or more of a sensor circuit 210, a signal processor circuit 220, a detector circuit 230, a controller circuit 240, and a user interface 250. In some examples, the respiratory monitoring system 200 may additionally include a therapy circuit 260 configured to deliver therapy to the patient to treat a respiratory disease or to prevent worsening of a respiratory condition. At least a portion of the respiratory monitoring system 200 may be implemented within the AMD 110, distributed between two or more implantable or wearable medical devices, or distributed between the AMD 110 and the external system 125.

The sensor circuit 210 may include a respiratory sounds sensor circuit 212 and an optional respiratory phase detector 214. The respiratory sounds sensor circuit 212 may include a sense amplifier circuit coupled to at least one physiological sensor to sense one or more physiological signals indicative of respiratory sounds (hereinafter referred to as the "respiratory sounds signals"). The respiratory sounds may include one or more of lung sounds, tracheal sounds, or bronchial sounds, among other sounds from the respiratory system. The physiological sensor may include one or more electrodes such as the electrodes on the system 108, or one or more implantable, wearable, holdable, or other ambulatory physiological sensors disposed at the patient's thorax or abdomen. The respiratory sounds signals include intrinsic physiological signals such as sensed during intrinsic cardia rhythm or voluntary breathing, evoked physiological responses such as during cardiac, pulmonary, or neural stimulation, or when the patient undergoes physiological activities.

Various physiological sensors may be used for sensing the respiratory sounds signals, which may include accelerometers, microphone sensors, pressure sensors, flow sensors, impedance sensors, respiration sensors, temperature sensors, or chemical sensors, among others. Accordingly, the respiratory sounds signals may include an acceleration signal, an acoustic signal, a thoracic impedance signal, a cardiac impedance signal, an arterial pressure signal, a pulmonary artery pressure signal, or an intracardiac pressure signal, among others. The sensor circuit 210 may additionally include one or more physiological sensors to sense electrocardiograph (ECG), an electrogram (EGM), a coronary blood temperature signal, a blood oxygen saturation signal, central venous pH value, a heart sounds (HS) signal, a posture signal, a physical activity signal, or a biomarker signal, among others. In some examples, the respiratory sounds sensor circuit 212 may be coupled to a storage device for storing the respiratory sounds signals, such as an external programmer, an electronic medical record (EMR) system, or a memory unit, among other devices.

The optional respiratory phase detector 214 may be coupled to one of an accelerometer, an impedance sensor, or a flow sensor to sense a respiration signal, and detect from the respiration signal a respiratory phase within a respiratory cycle. The respiratory phase may include an inspiration phase, an expiration phase, an apneic phase, a hypopneic phase, a transitional phase from inspiration to expiration, or a transitional phase from expiration to inspiration. In some examples, the respiratory phase may include a specified portion of the inspiration, expiration, or transitional phase of respiration with respect to a reference time of respiration, such as end of inspiration or end of expiration. The respiratory phase detector 214 may be coupled to the same sensor for sensing the physiological signals indicative of the respiratory sounds, process the physiological signal to extract a low-frequency envelop representing cyclic respiration rhythm, and detect from the envelop signal the desired respiratory phase, such as when the amplitude of the sensed respiration signal falls within a specified range.

The signal processor circuit 220, coupled to the sensor circuit 210, may include a spectral analyzer circuit 222 to generate from the sensed respiratory sounds signal a first spectral content (PS1) within a first frequency band (B1) and a second spectral content (PS2) within a second frequency band (B2). The second frequency band B2 may have a higher center frequency than the first frequency band B1. By way of non-limiting example, the first frequency band B1 may be in a range of approximately 100-300 Hz, and the second frequency band B2 may be in a range of 800-1200 Hz.

The spectral analyzer circuit 222 may generate a power spectrum representation of the respiratory sounds signal in a frequency domain or other transformed domain. The power spectrum representation may include magnitude of the power spectrum at a broad frequency range that includes at least both the frequency bands B1 and B2. The first and second spectral contents PS1 and PS2 may be determined as the magnitude of the power spectrum within the respective frequency bands B1 and B2. Alternatively, the spectral analyzer circuit 222 may include filter circuits, such as a first band-pass filter (BPF1) with cutoff frequencies matching the first frequency band B1, and a second band-pass filter (BPF2) with cutoff frequencies matching the second frequency band B2. The first spectral content PS1 may be determined as the power of the band-pass filtered respiratory sounds signal through the filter BFP1, and the second spectral content PS2 may be determined as the power of the band-pass filtered respiratory sounds signal through the filter BFP2.

The spectral analyzer 222 may optionally be coupled to the respiratory phase detector 214, and use a portion of the respiration sounds signal during the detected respiratory phase to generate the first and second spectral contents. When the respiratory sounds signal and the respiration signal are separately sensed using different physiological sensors or sensing circuits, the respiratory sounds signal may be synchronized to the respiration signal. In an example, a response delay between the sensing of the respiratory sounds signal and the sensing of respiration signal may be determined such as by using synchronization pulse. The synchronization of the respiratory sounds signal to the respiration signal may include adjusting the timings of the respiratory sounds signal based on the response delay. The portion of the synchronized respiratory sounds signal during inspiration phase of multiple respiration cycles may be ensemble-averaged, and the spectral contents PS1 and PS2 may be computed from spectral analysis of the ensemble-averaged respiratory sounds signals. In another example, spectral analysis may be performed on each of a plurality of synchronized respiratory sounds signals during inspiration phase. An ensemble average of the resultant spectra may be computed, and the spectral contents PS1 and PS2 may be determined from the ensemble-average spectrum. Examples of the spectral analyzer and the generation of the first and second spectral contents are discussed below, such as with reference to FIGS. 3A-B.

The detector circuit 230, coupled to the signal processor circuit 220, may include a respiratory anomaly indicator generator 232 to generate a respiratory anomaly indicator indicating a status of a target respiratory condition, such as presence, onset, termination, improvement, or worsening of a target respiratory condition. The respiratory anomaly indicator may be generated using at least the first and second spectral contents PS1 and PS2. In an example, the respiratory anomaly indicator may be computed as a relative measure between the PS1 and PS2. In another example, one or both of the spectral contents PS1 and PS2 may be compared to respective reference spectrum, and the respiratory anomaly indicator may be computed as a relative deviation of one or both of the PS1 and PS2 from the reference spectrum. The detector circuit 230 may include a threshold detector 234 to detect if respiratory anomaly indicator exceeds a specified threshold, and a diagnostic of respiratory disease may be generated. Examples of the detector circuit for detecting the target respiratory condition are discussed below, such as with reference to FIGS. 4A and 4B.

One or more of the signal processor circuit 220 or the detector circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the sensor circuit 210. Alternatively, the microprocessor circuit may be a general purpose processor that may receive and execute a set of instructions of performing the functions, methods, or techniques described herein.

The signal processor circuit 220 or the detector circuit 230 may include circuit sets comprising one or more other circuits or sub-circuits. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The controller circuit 240 may control the operations of the sensor circuit 210, the signal processor circuit 220, the detector circuit 230, the user interface 250, and the data and instruction flow between these components. The user interface 250 may include an output unit to generate a human-perceptible presentation of diagnostic information, such as a display of the respiratory anomaly indicator. The output unit may generate an alert if the respiratory anomaly indicator indicates presence of a new respiratory disease (e.g., an episode of asthma attack or an event of COPD), or worsening of an existing respiratory disease. The output unit may display information including the respiratory sounds signals, the first and second spectral contents, or a comparison between the spectral contents and reference spectra, among others. The information may be presented in a table, a chart, a diagram, or any other types of textual, tabular, or graphical presentation formats, for displaying to a system user. The presentation of the output information may include audio or other human-perceptible media format. In various examples, the output unit may provide the respiratory anomaly indicator to another process such as to assess patient health status or to recommend or titrate a therapy. The user interface 250 may include input device to enable a system user such as a clinician to program the parameters used for sensing the physiological signals, generating the spectral contents at respective frequency bands, or generating the respiratory anomaly indicator for detecting the target respiratory condition. Examples of the input device may include keyboard, on-screen keyboard, mouse, trackball, touchpad, touch-screen, or other pointing or navigating devices. In an example, at least a portion of the user interface 250 may be implemented in the external system 120.

In some examples, the respiratory monitoring system 200 may additionally include a therapy circuit 260 that is configured to deliver a therapy to the patient. The therapy may be triggered by a command signal in response to the respiratory anomaly indicator satisfying a specified condition. Examples of the therapy may include electrostimulation therapy delivered to cardiac or pulmonary tissue, heart, a nerve tissue, other target tissues in response to the detection of the target physiological event, or drug therapy including delivering drug to a tissue or organ. In some examples, the respiratory anomaly indicator may be used to modify an existing therapy, such as adjusting a stimulation parameter or drug dosage.

Figure 3A:
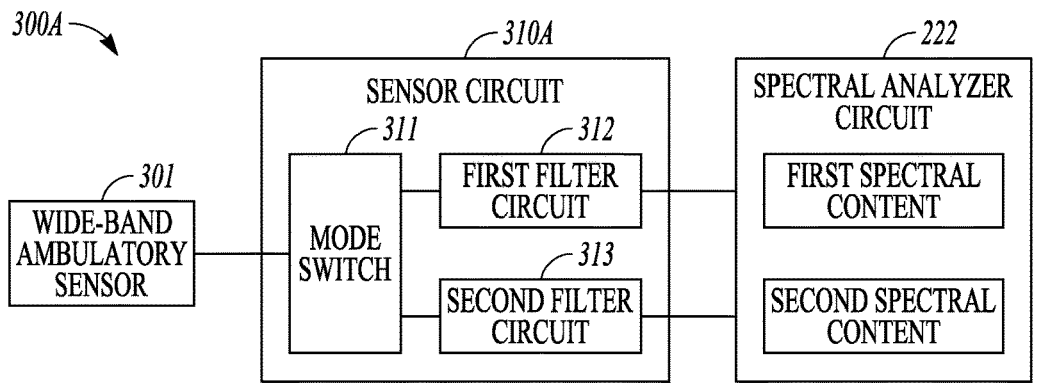
FIGS. 3A-B illustrate generally examples of a portion of a system for generating spectral contents from a respiratory sounds signal.
Figure 3B:
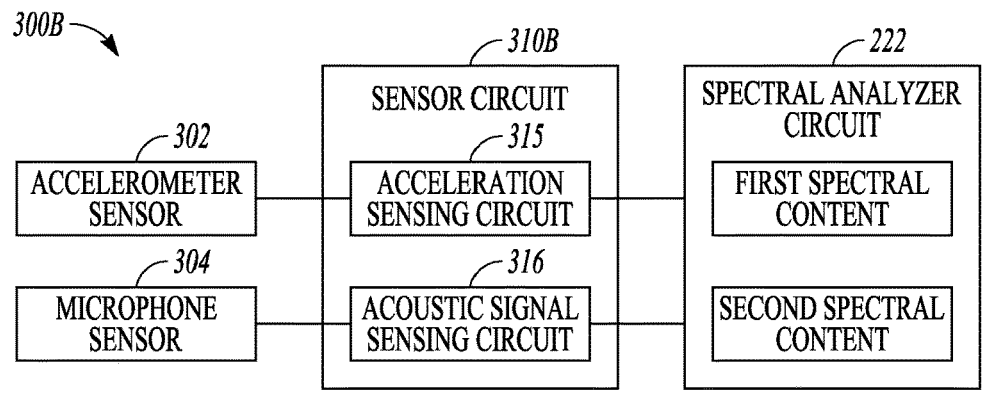

FIGS. 3A-B illustrate generally examples of portions of systems for generating spectral contents from a respiratory sounds signal. The system portion 300A in FIG. 3A and the system portion 300B in FIG. 3B may each be an embodiment of corresponding portions of the respiratory monitoring system 200. The system portion 300A may include a sensor circuit 310A coupled to a broadband ambulatory sensor 301. The broadband ambulatory sensor 301 may have a frequency response over a bandwidth that covers at least the first and second frequency bands B1 and B2, and is able to sense a broadband respiratory sounds signal. The sensor circuit 310A may include one or more filter circuits (such as bandpass filters) to selectively magnify certain frequency components of interest (such as the first frequency band B1 and the second frequency band B2) from the broadband respiratory sounds signal, and to suppress frequency components outside the frequency bands of interest. As an example illustrated in FIG. 3A, the broadband ambulatory sensor 301 may selectably operate in a first operating mode or a second operating mode. The sensor circuit 310A, which may be an embodiment of the sensor circuit 210 in FIG. 2, may include a mode switch 311 that may select between the first and second operating modes. The mode switch 311 may be actuated automatically such as according to a pre-determined instruction, or may be manually operated by a system user such as via the user interface 250. If the mode switch 311 is switched to the first operating mode, then a first filter circuit 312 is communicatively connected to the broadband ambulatory sensor 301. The first filter circuit 312 may have a frequency response including a passband substantially matching the first frequency band B1, and may magnify the frequency components of the respiratory sounds signal at the first frequency band B1 with a gain higher than frequencies outside the first frequency band B1. If the mode switch 311 is switched to the second operating mode, then a second filter circuit 313 may be communicatively connected to the broadband ambulatory sensor 301 to sense the respiratory sounds signal. The second filter circuit 313 may have a frequency response including a passband substantially matching the second frequency band B2, and may magnify the frequency components of the respiratory sounds signal at the second frequency band B2 with a gain higher than frequencies outside the second frequency band B2. The output of the second filter circuit 313 is a second filtered signal $X2(t)$.

The first filtered signal $X1(t)$ from the first filter circuit 312 and the second filtered signal $X(2)$ from the second filter circuit 313 may be used by the spectral analyzer circuit 222 to compute the first and second spectral contents PS1 and PS2, respectively. Because the first filter circuit 312 substantially magnifies the frequency content at the frequency band B1 and substantially suppresses other frequencies, the signal power of the filtered respiration sounds signal $X1(t)$ is dominated by the power at frequency band B1. Likewise, as the second filter circuit 313 substantially magnifies the frequency content at the frequency band B2 and substantially suppresses frequency components outside the frequency band B2, the signal power of the filtered respiration sounds signal $X2(t)$ is dominated by the power at frequency band B2. The spectral analyzer 222 may generate the first spectral content PS1 based on the signal power of $X1(t)$, and the second spectral content PS2 based on the signal power of $X2(t)$. The power spectral contents PS1 and PS2 may then be used by the detector circuit 230 to generate the respiratory anomaly indicator.

The system portion 300B as illustrated in FIG. 3B may include a sensor circuit 310B coupled to an accelerometer sensor 302 and a microphone sensor 304. The accelerometer sensor 302 and the microphone sensor 304 may be implantable or wearable sensors that are separately positioned at different thoracic or abdominal locations. Alternatively, the accelerometer sensor 302 and the microphone sensor 304 may be encapsulated together and positioned at substantially close locations at the thorax or abdomen.

The sensor circuit 310B may include an acceleration sensing circuit 315 coupled to the accelerometer sensor 302 to sense an acceleration signal $X_{XL}(t)$, and an acoustic signal sensing circuit 316 coupled to the microphone sensor 304 to sense an acoustic signal $X_{AC}(t)$. The spectral analyzer 222 may generate the first power spectral content PS1 based on the signal power of $X_{XL}(t)$, and generate the second power spectral content PS2 based on the signal power of $X_{AC}(t)$. The acceleration sensing circuit 315 may be configured to have a significantly higher gain in the first frequency band B1, such as between approximately 100 and 300 Hz, than other frequency bands, such that energies of the acceleration signal $X_{XL}(t)$ may be dominated by the first frequency band B1. Similarly, the acoustic signal sensing circuit 316 may be configured to have a significantly higher gain in the second frequency band B2, such as between approximately 800 and 1200 Hz, than other frequency bands, such that energies of the acoustic signal $X_{AC}(t)$ may be dominated by the second frequency band B2. Therefore, the first spectral content PS1 may be approximated by the signal power of $X_{XL}(t)$, and the second spectral content PS2 may be approximated by the signal power of $X_{AC}(t)$. The power spectra PS1 and PS2 may then be used by the detector circuit 230 to generate the respiratory anomaly indicator.

Figure 4A:
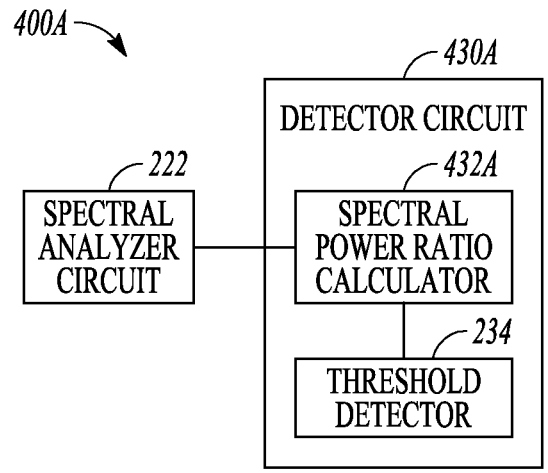
FIGS. 4A-B illustrate generally examples of a portion of a system for detecting a target respiratory condition based on spectral contents from a respiratory sounds signal.
Figure 4B:
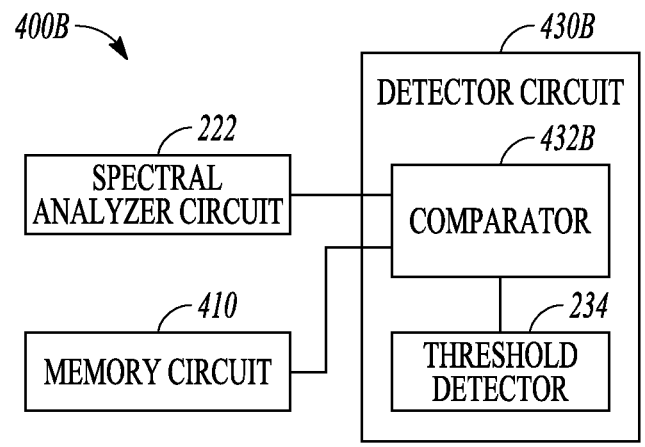

FIGS. 4A-B illustrates generally examples of portions of a system for detecting a target respiratory condition based on spectral contents from a respiratory sounds signal. The system portion 400A in FIG. 4A and the system portion 400B in FIG. 4B may each be an embodiment of corresponding portions of the respiratory monitoring system 200. The system portion 400A may include a detector circuit 430A, which may be an embodiment of the detector circuit 230 in FIG. 2. The detector circuit 430A may include a spectral power ratio calculator 432A coupled to the spectral analyzer circuit 222 and configured to compute a spectral power ratio ($R_{PS}$) of one of the spectral contents PS1 or PS2 to the other of the spectral contents PS1 or PS2. The spectral power ratio $R_{PS}$ may be an embodiment of the respiratory anomaly indicator. In an example, the spectral power ratio may be computed between a statistical measure of the PS1 over the first frequency band B1 and a statistical measure of the PS2 over the second frequency band B2. Examples of the statistical measure may include total power such as an integral or sum of the spectra at a plurality of frequencies within the respective frequency band (B1 or B2) or a specified portion within the respective frequency band, an average power such as the total power normalized by the bandwidth over which the total power is computed, or a representative power at a specified frequency such as the center frequency within the respective frequency band, among other statistical measurements. The threshold detector 234 may compare the spectral power ratio $R_{PS}$ to a threshold to detect an onset or worsening of a respiratory condition. In an example, the spectral power ratio $R_{PS}$ may be computed as $R_{PS}$=PS2/PS1, that is, a ratio of the power at the second higher frequency band B2 to the power at the first lower frequency band B1. An increase in the ratio $R_{PS}$, which may be a result of an increase in the spectral power PS2 at the higher frequency band B2 and/or a decrease in the spectral power PS1 at the lower frequency band B1, may indicate presence of asthma attack, or worsening of respiratory condition such as COPD, bronchiectasis, or acute bronchitis. The threshold detector 234 may detect the onset or worsening of a target respiratory condition in response to the spectral power ratio $R_{PS}$=PS2/PS1 exceeding a specified threshold.

The system portion 400B as illustrated in FIG. 4B may include a detector circuit 430B, which may be an embodiment of the detector circuit 230 in FIG. 2. The detector circuit 430B may include a comparator 432B coupled to the spectral analyzer circuit 222 and a memory circuit 410. The memory circuit 410 may store reference spectra of respiratory sounds, including a first reference spectrum rPS1 within the first frequency band B1 and a second reference spectrum rPS2 within the second frequency band B2. The reference spectra may be generated from spectral analysis of a baseline respiratory sounds signal sensed on a known condition such as when the patient is free of target respiratory anomaly, or in a stable respiratory condition without indications of worsening of an existing respiratory disease. The spectral analysis, such as generation of the first and second reference spectra rPS1 and rPS2, may be performed by the sensor circuit 210 and the signal processor circuit 220, or any variants thereof. The resulting reference spectra rPS1 and rPS2 may be stored in the memory circuit 410.

The comparator 432B may generate the respiratory anomaly indicator using a comparison of the spectral contents of the respiratory sounds generated at the spectral analyzer circuit 222 and the reference spectra retrieved from the memory circuit 410. In an example, the comparator 432 may generate the respiratory anomaly indicator in response to the first spectral content PS1 having a lower spectral power than the first reference spectrum rPS1 by a specified margin. In another example, the comparator 432 may generate the respiratory anomaly indicator in response to the second spectral content PS2 having a higher spectral power than the second reference spectrum rPS2 by a specified margin. The respiratory anomaly indicator may accordingly be computed as a relative measure between PS1 and rPS1, or between PS2 and rPS2. Examples of the relative measure may include a difference, a percentage difference, or a ratio, among other measures. The respiratory anomaly indicator may alternatively be computed using a combination of the relative measure between PS1 and rPS1 and the relative measure between PS2 and rPS2, such as a sum of the differences (rPS1−PS1) and (PS2−rPS2).

In an example, the comparator 432 may generate the respiratory anomaly indicator based on a comparison of the spectral power ratio between the first spectral content PS1 and the second spectral content PS2 and a reference spectral power ratio between the first reference spectrum rPS1 and the second reference spectrum rPS2. For example, the respiratory anomaly indicator may be generated in response to the spectral power ratio PS1/PS2 falling below the reference spectral power ratio rPS1/rPS2 by a specified margin ($\delta$), that is, rPS1/rPS2−PS1/PS2>$\delta$. In another example, the respiratory anomaly indicator may be generated in response to the spectral power ratio PS2/PS1 exceeding the reference spectral power ratio rPS2/rPS1 by a specified margin ($\delta'$), that is, PS2/PS1−rPS2/rPS1>$\delta'$. The respiratory anomaly indicator may accordingly be computed as a difference between the spectral power ratio and the reference spectral power ratio.

The threshold detector 234 may compare the respiratory anomaly indicator generate at the comparator 432B to a specified threshold to detect an onset or worsening of a respiratory condition. For example, an episode of asthma attack or a worsened condition of COPD may be declared if PS1 falls below rPS1 by a specified threshold, if PS2 exceeds rPS2 by a specified threshold, or if PS2/PS1 exceeds rPS2/rPS1 by a specified threshold, among other criteria based on the respiratory anomaly indicator generate at the comparator 432B.

Figure 5:
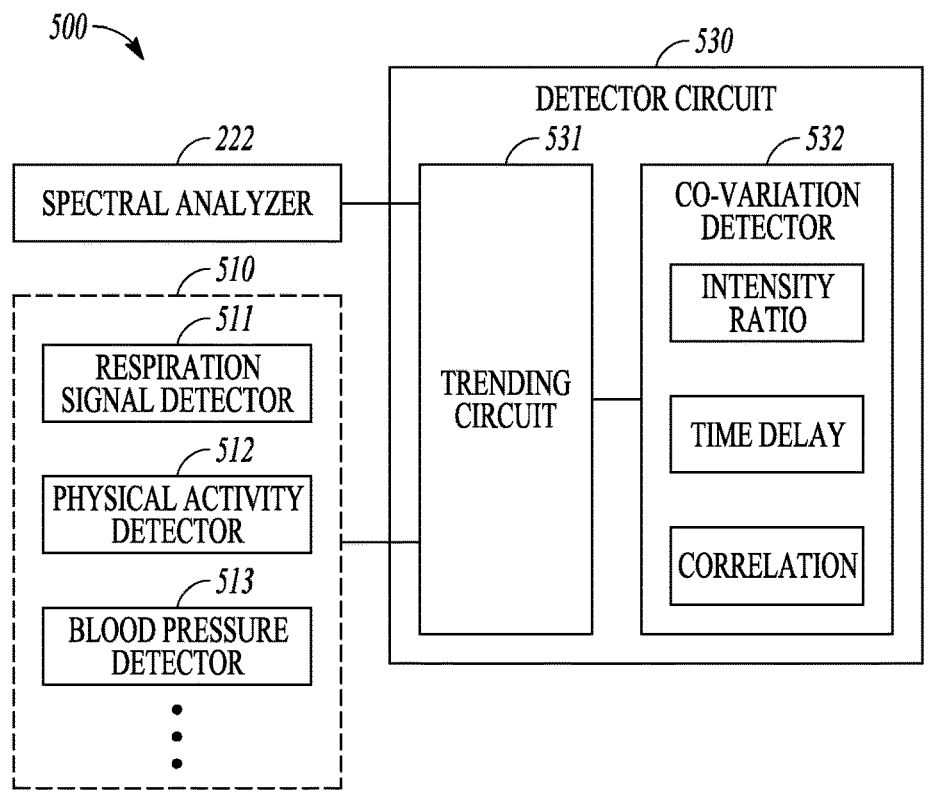
FIG. 5 illustrates generally an example of a portion of a system for detecting a target respiratory condition based on spectral contents from a respiratory sounds signal and other physiological information.

FIG. 5 illustrates generally an example of a portion of a system 500 for detecting a target respiratory condition based on spectral contents from a respiratory sounds signal and other physiological information. The system portion 500 may be an embodiment of corresponding portions of the respiratory monitoring system 200. The system portion 500 may include a detector circuit 530 coupled to the spectral analyzer 222 and one or more physiological detectors 510 each configured to detect a physiological parameter different from the spectral contents of respiratory sounds. By way of non-limiting example, the physiological detectors 510 may include one or more of a respiration signal detector 511, a physical activity detector 512, or a blood pressure detector 513, among others. The respiration signal detector 511 may be coupled to a respiration signal sensor circuit configured to sense a respiration signal using a thoracic impedance sensor, an accelerometer sensor, or a flow sensor. The respiration signal detector 511 may detect from the respiration signal one or more respiration parameters including a tidal volume, a respiration rate, a minute ventilation, or a rapid-shallow breathing index (RSBI) computed as a ratio of a respiratory rate measurement to a tidal volume measurement. The physical activity detector 512 may be coupled to an activity sensor such as an accelerometer to detect one or more of activity intensity, activity duration, posture, or a change of posture, among others. The blood pressure detector 513 may be coupled to a pressure sensor to detect systemic blood pressure or cardiac pressure at one or more heart chambers or cardiac blood vessels.

The detector circuit 530 may include a trending circuit 531 and a co-variation detector 532. The trending circuit 531, coupled to the spectral analyzer 222 and one or more of the physiological detectors 510, may track the temporal changes of the spectral contents of the respiratory sounds such as the first and second spectral contents PS1 and PS2 and the temporal changes of the one or more physiological parameters detected from the physiological detectors 510. In an example, the trending circuit 531 may generate a trend of the spectral contents PS1 or PS2, or a trend of relative measure between PS1 and PS2 such as a trend of spectral power ratio PS2/PS1. Likewise, the trending circuit 531 may generate one or more trends over time of the physiological parameters such as a trend of respiration rate, a trend of tidal volume, a trend of physical activity intensity, or a trend of blood pressure, among others.

The co-variation detector 532 may generate a co-variation indicator from the one or more trends of the physiological parameters and the trends of the spectral contents of the respiratory sounds. In an example, the co-variation indicator may include a ratio of the spectral contents of the respiratory sounds (such as PS1, PS2, or a relative measure between PS1 and PS2) to the physical activity intensity. In an example, the co-variation indicator may include a time interval between a peak of PS1 or PS2 trend and a peak of the physical activity intensity within the specified time period. Peak of PS1 or PS2 trend may correspond to peak intensity of respiratory distress such as asthma. A short time interval between the peak of PS1 or PS2 trend and the physical activity peak intensity may indicate an exercise-induced bronchoconstriction such as exercise-induced asthma, while a longer time interval may indicate non-exercise induced or chronic respiratory distress. In another example, the co-variation indicator may include a ratio of the respiratory anomaly indicator (such as one of the spectral power ratios or relative measures with respect to reference spectral contents as previously discussed with reference to FIGS. 4A-B) to the physical activity intensity.

In various examples, the co-variation indicator may include a pulmonary distress index based on the respiratory sounds signal and one or more respiration signal parameters such as respiration rate, tidal volume, minute ventilation, or RSBI. An example of the pulmonary distress index may include a correlation between the sensed respiratory sounds signal and the respiration signal during a specified respiratory phase, or a correlation between the trend of a spectral content (such as a trend of PS1 or a trend of PS2) and a trend of a respiration signal parameter. The co-variation detector 532 may additionally classify the respiratory disease into one of two or more categories of pulmonary distress using the pulmonary distress index. The categories of pulmonary distress may indicate different degrees, causes, or locations of pulmonary distress. Additionally or alternatively, the classification of the respiratory disease may be performed by categorizing the respiratory anomaly indicator into different levels of severity of the pulmonary distress such as by using a plurality of thresholds.

Figure 6:
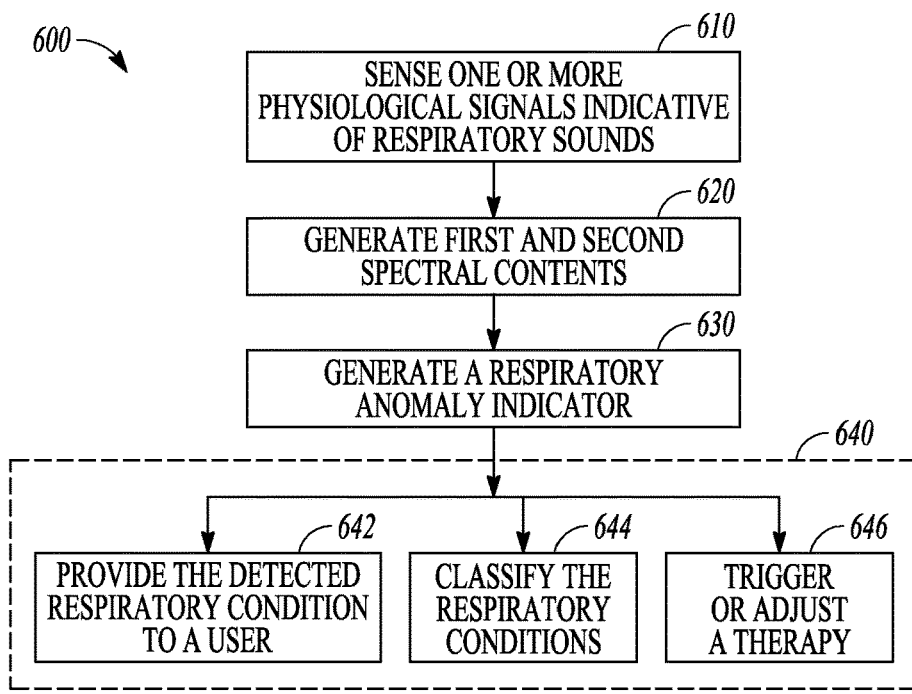
FIG. 6 illustrates generally an example of a method for monitoring respiration and detecting respiratory anomaly.

FIG. 6 illustrates generally an example of a method 600 for monitoring respiration and detecting respiratory anomaly, such as wheezing, asthma, bronchoconstriction, COPD, bronchiectasis, acute bronchitis, pulmonary fibrosis, pneumoconiosis, acute respiratory distress syndrome, or sleep apnea. The method 600 may be implemented in and executed by an ambulatory medical device such as an implantable or wearable medical device, or in a remote patient management system. In an example, the method 600 may be executed by the respiratory monitor 160 or by the external system 125. In an example, the method 600 may be implemented in and executed by the respiratory monitoring system 200 or any embodiments thereof.

The method 600 begins at 610 by sensing one or more physiological signals indicative of respiratory sounds (referred to as the "respiratory sounds signals"). The respiratory sounds may be sensed using one or more implantable, wearable, holdable, or other ambulatory physiological sensors disposed at the patient's thorax or abdomen. Examples of the physiological sensors for sensing the respiratory sounds signals may include accelerometers, microphone sensors, pressure sensors, flow sensors, impedance sensors, respiration sensors, temperature sensors, or chemical sensors, among others. Additional physiological signals may also be sensed at 610, including a ECG, a EGM, a coronary blood temperature signal, a blood oxygen saturation signal, central venous pH value, a heart sound signal, a posture signal, a physical activity signal, or a biomarker signal, among others.

At 620, spectral analysis of the respiratory sounds signals may be performed, such as via a spectral analyzer 222 as illustrated in FIG. 2, to generate a first spectral content (PS1) within a first frequency band (B1) and a second spectral content (PS2) within a second frequency band (B2). The second frequency band B2 may have a higher center frequency than the first frequency band B1. The first frequency band B1 may be in a range of approximately 100-300 Hz, and the second frequency band B2 may be in a range of 800-1200 Hz. The respiratory sounds signals may be filtered using a filter bank such as including a first band-pass filter (BPF1) with cutoff frequencies matching the first frequency band B1 and a second band-pass filter (BPF2) with cutoff frequencies matching the second to frequency band B2. The first spectral content PS1 may be determined as the power of the band-pass filtered respiratory sounds signal through the filter BFP1, and the second spectral content PS2 may be determined as the power of the band-pass filtered respiratory sounds signal through the filter BFP2.

In an example, the respiratory sounds signals may be sensed at 610 using a broadband ambulatory sensor having a frequency response over a bandwidth that covers at least the first and second frequency bands B1 and B2, such as the sensor 301 as illustrated in FIG. 3. The broadband ambulatory sensor may be configured to operate in a first operating mode, and a first filtered signal X1(t) may be generated using a first filter circuit having a frequency response including a passband substantially matching the first frequency band B1. The broadband ambulatory sensor may additionally or alternatively be configured to operate in a second operating mode, and a second filtered signal X2(t) may be generated using a second filter circuit having a frequency response including a passband substantially matching the second frequency band B2. As the signal power of the filtered respiration sounds signal X1(t) is dominated by the power at frequency band B1, and the signal power of the filtered respiration sounds signal X2(t) is dominated by the power at frequency band B2, at 620, the spectral content PS1 may be approximated by the signal power of X1(t), and the spectral content PS2 may be approximated by the signal power of X2(t).

In another example, the respiratory sounds signals at 610 may include at least an acceleration signal $X_{XL}(t)$ such as sensed from an accelerometer sensor, and an acoustic signal $X_{AC}(t)$ such as sensed from an acoustic sensor. The acceleration sensor may be tuned to have a significantly higher gain in the first frequency band B1, such as between approximately 100 and 300 Hz, than other frequency bands, such that energies of the acceleration signal $X_{XL}(t)$ may be dominated by the first frequency band B1. The acoustic sensor may be tuned to have a significantly higher gain in the second frequency band B2, such as between approximately 800 and 1200 Hz, than other frequency bands, such that energies of the acoustic signal $X_{AC}(t)$ may be dominated by the second frequency band B2. At 620, the first spectral content PS1 may be approximated by the signal power of $X_{XL}(t)$, and the second spectral content PS2 may therefore be approximated by the signal power of $X_{AC}(t)$.

At 630, a respiratory anomaly indicator may be generated using at least the first and second spectral contents PS1 and PS2. The respiratory anomaly indicator may indicate status of a target respiratory condition, such as presence, onset, termination, improvement, or worsening of a target respiratory condition. The respiratory anomaly indicator may be computed as a relative measure between the PS1 and PS2. The respiratory anomaly indicator may alternatively be determined using one or both of the spectral contents PS1 and PS2 and a reference spectrum. Examples of methods of detecting respiratory anomaly using spectral contents of the respiratory sounds are discussed below, such as with reference to FIG. 7.

The respiratory anomaly indicator may be provided to a user or a process at 640. At 642, a human-perceptible presentation of the respiratory anomaly indicator may be generated, and displayed such as on the user interface 250. In an example, an alert may be generated if the respiratory anomaly indicator indicates presence of a new episode of asthma attack or COPD, or worsening of an existing respiratory disease. The human-perceptible presentation may additionally include the respiratory sounds signals, the first and second spectral contents, or a comparison between the spectral contents and reference spectra, among others. The information may be presented in a table, a chart, a diagram, or any other types of textual, tabular, or graphical presentation formats, for displaying to a system user. The presentation of the output information may include audio or other human-perceptible media format.

At 644, the respiratory anomaly indicator may be used to trigger a classification of the respiratory anomaly into one of two or more categories of pulmonary distress. The categories of pulmonary distress may indicate different degrees, causes, or locations of pulmonary distress. In an example, the classification may be based on comparison of the respiratory anomaly indicator with a plurality of thresholds each defining a particular degree of severity of the pulmonary distress. In another example, the classification may be based on trends of the spectral contents of the respiratory sounds (such as PS1, PS2, or a relative measure between PS1 and PS2) and one or more trends of the physiological parameters. In an example, the co-variation may include a ratio of PS1 or PS2 to the physical activity intensity. In an example, the co-variation may include a time interval between a peak of PS1 or PS2 and a peak of the physical activity intensity within a specified time period. In yet another example, the co-variation may include a correlation between the sensed respiratory sounds signal and the respiration signal during a specified respiratory phase, or a correlation between the trend of a spectral content and a trend of a respiration signal parameter.

At 646, the respiratory anomaly indicator may additionally or alternatively be used to trigger a therapy delivered to the patient or to modify an existing therapy, such as via the therapy circuit 260. The therapy may be triggered by a command signal in response to the respiratory anomaly indicator satisfying a specified condition. Examples of the therapy may include electrostimulation therapy delivered to cardiac or pulmonary tissue, heart, a nerve tissue, other target tissues in response to the detection of the target physiological event, or drug therapy including delivering drug to a tissue or organ.

Figure 7:
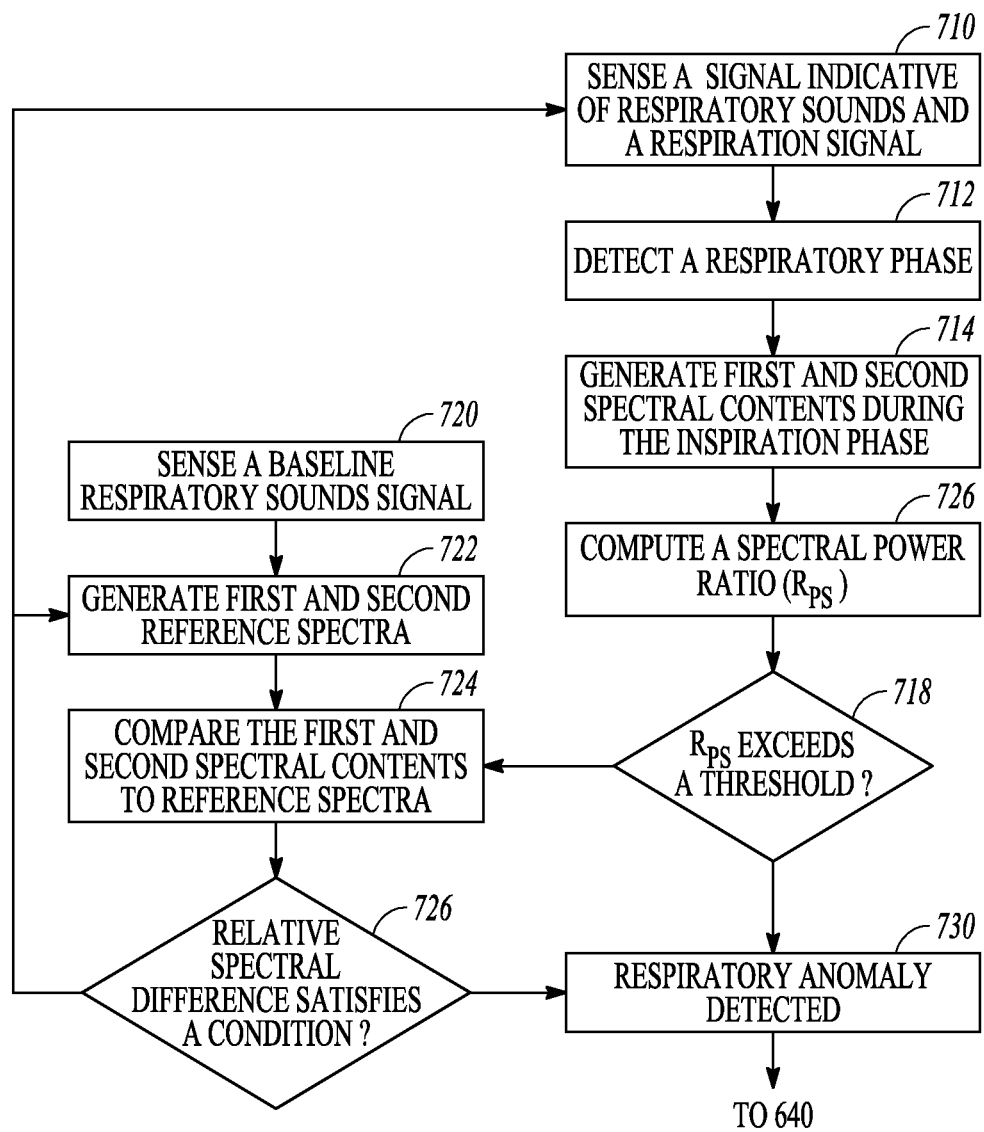
FIG. 7 illustrates generally an example of a method for detecting respiratory anomaly using spectral contents of the respiratory sounds.

FIG. 7 illustrates generally an example of a method 700 for detecting respiratory anomaly using spectral contents of the respiratory sounds. The method 700 may be executed by the respiratory monitor 160 or by the external system 125. In an example, the method 700 may be implemented in and executed by the respiratory monitoring system or any embodiments thereof.

The method 700 begins at 710 by sensing a physiological signal indicative of respiratory sounds (the "respiratory sounds signal") and a respiration signal. In an example, the respiratory sounds signal and the respiratory signal may be one common signal that includes information about the respiratory sounds and the respiratory periodicity and phases. In another example, the respiratory sounds signal and the respiratory signal may be separately sensed such as by using different physiological sensors. Similar to the step 610 of the method 600, the respiratory sounds signals may include a broadband signal including at least frequency contents at at least the frequency bands B1 and B2, or alternatively may include an acceleration signal $X_{XL}(t)$ and an acoustic signal $X_{AC}(t)$ which may be separately sensed using respective implantable, wearable, holdable, or otherwise ambulatory sensors.

At 712, a respiratory phase within a respiratory cycle may be detected from the respiratory signal. The respiratory phase may include an inspiration phase, an expiration phase, an apneic phase, a hypopneic phase, a transitional phase from inspiration to expiration, a transitional phase from expiration to inspiration, or a specified portion of the inspiration, expiration, or transitional phase of respiration with respect to a reference time.

At 714, spectral analysis of the respiratory sounds signal may be performed to generate first and second spectral contents, PS1 and PS2, during the inspiration phase. The respiratory sounds signal may be synchronized to the respiration signal, such that a portion of the respiration sounds signal during the inspiration phase of each respiration cycle are used to generate the spectral contents PS1 and PS2. The respiratory sounds signal may be synchronized to the respiration signal, and spectral analysis may be performed on the portion of the synchronized respiratory sounds signal during inspiration phase of multiple respiration cycles. An ensemble average of the resultant spectra may be computed, and the spectral contents PS1 and PS2 may be determined from the ensemble-average spectrum.

At 716, a spectral power ratio ($R_{PS}$) of one of the spectral contents PS1 or PS2 to the other of the spectral contents PS1 or PS2 may be computed. The spectral power ratio $R_{PS}$ may be a respiratory anomaly indicator and used for detect respiratory distress. In an example, the spectral power ratio $R_{PS}$ may be computed as a ratio of the power of PS2 to the power of PS1, that is $R_{PS}$=PS2/PS1. In some examples, the spectral power ratio may be computed as a ratio of statistical measure of PS2 within the frequency band B2 to statistical measure of PS1 within the frequency band B1.

The spectral power ratio $R_{PS}$, such as PS2/PS1, may be compared to a threshold at 718. An increase in the ratio $R_{PS}$, which may be a result of an increase in the spectral power PS2 at the higher frequency band B2 and/or a decrease in the spectral power PS1 at the lower frequency band B1, may indicate presence of asthma attack, or worsening of respiratory condition such as COPD, bronchiectasis, or acute bronchitis. If $R_{PS}$ exceeds the threshold, then respiratory anomaly is deemed detected at 730. The process can proceed to step 640 to provide the respiratory anomaly indicator, such as $R_{PS}$, to a user or a process.

If at 718 the $R_{PS}$ falls below the threshold, then the spectral contents (such as PS1, PS2, or a relative measure between PS1 and PS2) may be compared to reference spectra at 724. The reference spectra may be generated using a process including the steps 720 and 722, as illustrated in FIG. 7. A baseline respiratory sounds signal may be sensed at 720 when the patient is free of target respiratory anomaly or in a stable respiratory condition without indications of worsening of an existing respiratory disease. At 722, reference spectral contents may be generated from spectral analysis of the baseline respiratory sounds signal. The reference spectral contents may include a first reference spectrum rPS1 within the first frequency band B1 and a second reference spectrum rPS2 within the second frequency band B2. At 724, a respiratory anomaly indicator may be generated based on the comparison between the first and second spectral contents PS1 and PS2 to the reference spectra rPS1 and rPS2. The respiratory anomaly indicator may include a difference between the first spectral content PS1 and the first reference spectrum rPS1, a difference between the second reference spectrum rPS2 and the second spectral content PS2, or a combination (such as a sum) of the differences (rPS1−PS1) and (PS2−rPS2). The respiratory anomaly indicator may additionally or alternatively include a difference between the spectral power ratio PS2/PS1 and the reference spectral power ratio rPS2/rPS1, or between the spectral power ratio PS1/PS2 and the reference spectral power ratio rPS1/rPS2.

At 726, the respiratory anomaly indicator, such as one or more relative spectral differences as determined at 724, may be compared to respective thresholds to detect a respiratory anomaly. In various examples a respiratory anomaly is deemed detected at 730 if one or more of the following conditions are satisfied: PS1 has a lower spectral power than the first reference spectrum rPS1 by a specified margin; the PS2 has a higher spectral power than the second reference spectrum rPS2 by a specified margin; the sum of the differences (rPS1−PS1)+(PS2−rPS2) exceeds a threshold; the spectral power ratio PS1/PS2 falling below the reference spectral power ratio rPS1/rPS2 by a specified margin; or the spectral power ratio PS2/PS1 exceeding the reference power ratio rPS2/rPS1 by a specified margin, among others. The process can proceed to step 640 to provide the respiratory anomaly indicator, such as $R_{PS}$, to a user or a process. If the respiratory anomaly indicator fails to satisfy the specified condition at 726, then no respiratory anomaly is deemed detected, and the process may proceed to 710 to continue sensing the respiratory sounds signals and the respiration signal, or alternatively or additionally updating the reference spectra by sensing additional baseline respiratory sounds signal at 720.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for managing a respiratory disease in a patient, the system comprising:
    a sensor circuit including a sense amplifier coupled to at least one ambulatory or implantable physiological sensor to sense one or more physiological signals indicative of respiratory sounds, wherein the at least one ambulatory or implantable physiological sensor includes an accelerometer, and the one or more physiological signals include an acceleration signal sensed by the accelerometer;
    a signal processor circuit including a spectral analyzer circuit configured to generate from the sensed one or more physiological signals a first spectral content of respiratory sounds within a first frequency band and a second spectral content of respiratory sounds within a second frequency band, the second frequency band having a higher center frequency than the first frequency band;
    a detector circuit coupled to the signal processor circuit and configured to:
        receive at least one physiological parameter of the patient different from the first and the second spectral contents, the received at least one physiological parameter including a blood pressure parameter;
        calculate a correlation between (i) a change in at least one of the first spectral content or the second spectral content over time and (ii) a change in the received at least one physiological parameter including a change in the blood pressure parameter over time; and
        generate a respiratory anomaly indicator using the calculated correlation, the respiratory anomaly indicator indicating a status of chronic obstructive pulmonary disease (COPD) or asthma of the patient; and
    an output circuit configured to provide the respiratory anomaly indicator to a user or a process.

2. The system of claim 1, wherein:
    the at least one ambulatory or implantable physiological sensor has a frequency response over a bandwidth including the first and second frequency bands, and is configured to selectably operate in a first operating mode or a second operating mode; and
    the spectral analyzer circuit is configured to generate the first spectral content when the at least one ambulatory or implantable physiological sensor operates in the first operating mode, and to generate the second spectral content when the least one ambulatory or implantable physiological sensor operates in the second operating mode.

3. The system of claim 1, wherein:
    the sensor circuit includes a microphone sensor configured to sense an acoustic signal; and
    the spectral analyzer circuit is configured to generate the first spectral content from the acceleration signal, and to generate the second spectral content from the acoustic signal.

4. The system of claim 1, further comprising a respiratory sensor circuit configured to sense a respiration signal and to detect a respiratory phase within a respiratory cycle, and
    wherein the spectral analyzer circuit is configured to generate the first and second spectral contents using the sensed one or more physiological signals during the detected respiratory phase.

5. The system of claim 4, wherein the detector circuit is further configured to:
    generate a correlation between the sensed one or more physiological signals and the respiration signal during a specified respiratory phase; and
    classify the respiratory disease into one of two or more categories of pulmonary distress using the correlation.

6. The system of claim 1, wherein the detector circuit is configured to generate the respiratory anomaly indicator further using a spectral power ratio of one of the first or second spectral content to the other of the first or second spectral content.

7. The system of claim 1, comprising a memory circuit to store a reference spectral content of respiratory sounds, the reference spectral content including a first reference spectrum within the first frequency band and a second reference spectrum within the second frequency band, wherein the detector circuit is configured to generate the respiratory anomaly indicator further using one or more of the first or the second spectral content, the respiratory anomaly indicator indicating:
    the first spectral content having a lower spectral power than the first reference spectrum by a specified margin;
    the second spectral content having a higher spectral power than the second reference spectrum by a specified margin; or
    a ratio of the first spectral content to the second spectral content falling below a ratio of the first reference spectrum to the second reference spectrum by a specified margin.

8. The system of claim 1, wherein the received at least one physiological parameter further includes a physical activity intensity, the system further comprising a physical activity sensor configured to sense the physical activity intensity, wherein the detector circuit is configured to:
    trend over time the first or second spectral content of the respiratory sounds and the physical activity intensity; and
    generate the respiratory anomaly indicator using a correlation between the trended first or second spectral content of the respiratory sounds and the trended physical activity intensity.

9. The system of claim 8, wherein the detector circuit is configured to generate the anomaly indicator including further using at least one of:
    a ratio of the intensity of the first or second spectral contents of the respiratory sounds to the physical activity intensity;

a time interval between a peak of the intensity of the first or second spectral contents of the respiratory sounds and a peak of the physical activity intensity; or a ratio of the respiratory anomaly indicator to the physical activity intensity.

10. The system of claim 1, wherein the received at least one physiological parameter further includes a respiration parameter, and the detector circuit is configured to generate the respiratory anomaly indicator using a correlation between (i) the first or the second spectral content of the respiratory sounds and (ii) a change in the respiration parameter over time.

11. The system of claim 10, wherein the respiration parameter includes at least one of a respiration rate, a tidal volume, or a rapid-shallow breathing index.

12. A method for detecting a respiratory anomaly in a patient using a respiratory disease management system, the method comprising:

sensing, via an ambulatory or implantable physiological sensor including an accelerometer, one or more physiological signals indicative of respiratory sounds including an acceleration signal sensed by the accelerometer;

performing spectral analysis, via a spectral analyzer, on the sensed one or more physiological signals to generate a first spectral content of respiratory sounds within a first frequency band and a second spectral content of respiratory sounds within a second frequency band, the second frequency band having a higher center frequency than the first frequency band;

receiving at least one physiological parameter of the patient different from the first and the second spectral contents, the received at least one physiological parameter including a blood pressure parameter;

calculating a correlation between (i) a change in at least one of the first spectral content or the second spectral content over time and (ii) a change in the received at least one physiological parameter including a change in the blood pressure parameter over time;

generating a respiratory anomaly indicator using the calculated correlation, the respiratory anomaly indicator indicating a status of chronic obstructive pulmonary disease (COPD) or asthma of the patient; and providing the respiratory anomaly indicator to a user or a process.

13. The method of claim 12, wherein the spectral analysis includes:

configuring the ambulatory or implantable physiological sensor to operate in a first operating mode and generating the first spectral content when the sensor operates in the first operating mode;

configuring the ambulatory or implantable physiological sensor to operate in a different second operating mode and generating the second spectral content when the ambulatory or implantable physiological sensor operates in the second operating mode.

14. The method of claim 12, wherein:

sensing the one or more physiological signals includes sensing an acoustic signal via a microphone sensor; and performing the spectral analysis includes generating the first spectral content from the acceleration signal and generating the second spectral content from the acoustic signal.

15. The method of claim 12, further comprising sensing a respiration signal and detecting a respiratory phase within a respiratory cycle, and wherein the spectral analysis includes generating the first and second spectral contents using the sensed one or more physiological signals during the detected respiratory phase.

16. The method of claim 15, further comprising:

generating a correlation between the sensed one or more physiological signals and the respiration signal during a specified respiratory phase; and classifying the respiratory disease into one of two or more categories of pulmonary distress using the correlation.

17. The method of claim 12, wherein generating the respiratory anomaly indicator further includes using a spectral power ratio of one of the first or second spectral content to the other of the first or second spectral content.

18. The method of claim 12, further comprising generating a reference spectral content of respiratory sounds, the reference spectral content including a first reference spectrum within the first frequency band and a second reference spectrum within the second frequency band, wherein generating the respiratory anomaly indicator further includes using one or more of the first or the second spectral content, the respiratory anomaly indicator indicating:

the first spectral content having a lower spectral power than the first reference spectrum by a specified margin;

the second spectral content having a higher spectral power than the second reference spectrum by a specified margin; or a ratio of the first spectral content to the second spectral content falling below a ratio of the first reference spectrum to the second reference spectrum by a specified margin.

19. The method of claim 12, wherein the received at least one physiological parameter further includes a physical activity intensity, the method further comprising:

trending over time the first or second spectral contents of the respiratory sounds and the physical activity intensity; and generating the respiratory anomaly indicator using a correlation between the trended first or second spectral content of the respiratory sounds and the trended physical activity intensity.

* * * * *